United States Patent
Osborne et al.

(10) Patent No.: US 7,217,533 B2
(45) Date of Patent: May 15, 2007

(54) P38 MAPK PATHWAY PREDICTS ENDOCRINE-RESISTANT GROWTH OF HUMAN BREAST CANCER AND PROVIDES A NOVEL DIAGNOSTIC AND TREATMENT TARGET

(75) Inventors: C. Kent Osborne, Houston, TX (US); Rachel Schiff, Bellaire, TX (US); Jiang Shou, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 651 days.

(21) Appl. No.: 10/177,296

(22) Filed: Jun. 21, 2002

(65) Prior Publication Data

US 2003/0049660 A1    Mar. 13, 2003

Related U.S. Application Data

(60) Provisional application No. 60/299,824, filed on Jun. 21, 2001.

(51) Int. Cl.
*C12Q 1/00* (2006.01)
*G01N 33/53* (2006.01)
*G01N 33/567* (2006.01)
*G01N 33/48* (2006.01)
*G01N 33/00* (2006.01)
*G01N 1/00* (2006.01)
*C12N 9/00* (2006.01)

(52) U.S. Cl. .................. 435/7.23; 435/4; 435/7.1; 435/7.21; 435/183; 436/63; 436/64; 436/86; 436/174; 436/536

(58) Field of Classification Search ................ 435/183, 435/4, 7.1, 7.21, 7.23; 436/536, 174, 86, 436/63, 64

See application file for complete search history.

(56) References Cited

U.S. PATENT DOCUMENTS 5,836,905 A    11/1998   Lemelson et al.   ............ 604/21

FOREIGN PATENT DOCUMENTS

WO    WO 00/34788    6/2000

OTHER PUBLICATIONS

Lee et al. Inhibition of p38 MAP kinase as a therapeutic strategy. Immunopharmocology 47: 185-201, 2000.*
Gutierrez et al. Molecular Changes in Tamoxifen-Resistant Breast Cancer: Relationship Between Estrogen Receptor, HER-2, and p38 Mitogen -Activated Protein Kinase. Journal of Clinical Oncology 23(11): 2469-2476, Apr. 10, 2005.*
Dumas J, et al., 2002, "Synthesis and Pharmacological Characterization of a Potent, Orally Active p38 Kinase Inhibitor" *Bioorg Med Chem Letters* 12:1559-1562.
Massarweh S et al., 2002, "Inhibition of epidermal growth factor/HER2 receptor signaling using ZD1839 ('Iressa') restores tamoxifen sensitivity and delays resistance to estrogen deprivation in HER2-overexpression breast tumors" *Proceedings of ASCO* 21:33a (Abstract 130).
Osborne CK et al., 2002, "The estrogen receptor coactivator ALB1 (SRC3) in combination with HER-2 is a prognostic and predictive marker in patients with breast cancer" *Proceedings of ASCO* 21:33a (Abstract 129).
Shou J et al., 2002, "The selective epidermal growth factor receptor tyrosine kinase inhibitor ZD1839 ('Iressa') blocks estrogen receptor/growth factor cross-talk implicated in tamoxifen resistance in breast cancer" *American Association for Cancer Research*, 93rd Annual Meeting, Apr. 6-10, 2002, San Francisco CA (Abstract 4964).
Barone et al., 2001, "Inhhibition of p38 Mitogen-Activated Protein Kinase Provides Neuroprotection in Cerebral Focal Ischemia" *Med Res Rev.* 21(2):129-145.
Driggers PH et al., 2001, "The Proto-oncoprotein Brx Activates Estrogen Receptor β by a p38 Mitogen-activated Prot Kinase Pathway" *J. Biol. Chem.* 276(50):46792-46797.
Jacobs A et al., 2001, "Quantitative Kinetics of [$^{124}$I]FIAU in Cat and Man" *J Nucl Med* 42(3):467-475.
Legos et al., 2001, "SB 239063, a novel p38 inhibitor, attenuates early neuronal injury following ischemia" *Brain Res.* 892:70-77.
McLay LM et al., 2001, "The Discovery of RPR 200765A, a p38 MAP Kinase Inhibitor Displaying a Good Oral Anti-Arthritic Efficacy" *Bioorg Med Chem.* 9:537-554.
Shou J et al., 2001, "Onset of endocrine resistance in breast cancer is associated with increased active p38 MAPK" *Breast Cancer Res Treat* 69:254 (Abstract 272).
Katzenellenbogen BS et al., 2000, "Estrogen Receptors: Selective Ligands, Partners, and Distinctive Pharmacology" *Recent Progress In Hormones Res* 55:163-195.
Lee et al., 2000, "MEKK1 Activation of Human Estrogen Receptor α and Stimulation of the Agonistic Activity of 4-Hydroxytamoxifen in Endometrial and Ovarian Cancer Cells" , *Mol Endocrinol.* 14(11):1882-1896.
Schiff R et al., 2000, Oxidative Stress and AP-1 Activity in Tamoxifen-Resistant Breast Tumors *In Vivo*, *J Natl Cancer Inst* 92(23):1926-1934.

(Continued)

*Primary Examiner*—Alana M. Harris
(74) *Attorney, Agent, or Firm*—Baker Botts L.L.P.

(57) ABSTRACT

Acquired and de novo endocrine resistance are major clinical problems in the management of breast cancer patients. Though the antiestrogen tamoxifen prolongs disease-free and overall survival in the adjuvant setting, and induces remissions in over half of the patients with estrogen receptor positive metastatic disease, all patients eventually acquire tamoxifen resistance. Furthermore, many of the resistant tumors actually appear to be stimulated by tamoxifen just as they are by estrogens. The present invention provides methods of predicting endocrine resistance comprising detecting the biological activity and/or expression of p38 MAPK and/or AIB1. The invention further provides methods of reducing, reversing, or preventing endocrine resistance comprising contacting a breast or prostate tumor with a p38 MAPK pathway inhibitor.

38 Claims, 3 Drawing Sheets

OTHER PUBLICATIONS

Wunderbaldinger P et al., 2000, "New approaches for imaging in gene therapy" *Eur J Radiol* 34:156-165.

Thompson S et al., 1999, "MAP kinase-mediated signalling to nucleosomes and immediate-early gene induction", *Cell Dev. Biol.* 10:205-214.

Löfberg M et al., 1998, "Antimyosin Scintigraphy Compared with Magnetic Resonance Imaging in Inflammatory Myopathies" *Arch Neurol.* 55:987-993.

Osborne CK, 1998, "Tamoxifen In The Treatment of Breast Cancer", *N Engl J Med* 339(22):1609-1618.

Pierrat B et al., 1998, " RSK-B, a novel ribosomal S6 kinase family member, is a CREB kinase under dominant control of p38α mitogen-activate protein kinase (p38α$^{MAPK}$)" *J. Biol. Chem.* 273(45):29661-29671.

Cuenda A, et al., 1996, "Purification and cDNA cloning of SAPKK3, the major activator of RK/p38 in stress- and cytokine-stimulated monocytes and epithelial cells" *EMBO J.* 15(16):4156-4164.

Weigel N, 1996, "Steroid hormone receptors and their regulation by phosphorylation" *Biochem J* 319:657-667.

Kato S et al., 1995, "Activation of the Estrogen Receptor Through Phosphorylation by Mitogen-Activated Protein Kinase" *Science* 270:1491-1494.

Osborne et al., 1995, "Comparison of the Effects of a Pure Steroidal Antiestrogen With Those of Tamoxifen in a Model of Human Breast Cancer", *J Natl Cancer Inst* 87(10):746-750.

Fujimoto N et al., 1994, "Alteration in the Agonist/Antagonist Balance of Antiestrogens by Activation of Protein Kinase A Signaling Pathways in Breast Cancer Cells: Antiestrogen Selectivity and Promoter Dependence" *Mol Endocrinol.* 8(3):296-304.

Osborne CK et al., 1994, "Mechanisms of tamoxifen resistance", *Breast Cancer Res Treat.* 32:49-55.

Encarnación CA et al., 1993, "Measurement of steroid hormone receptors in breast cancer patients on tamoxifen" *Breast Cancer Res. Treat.* 26:237-246.

Early Breast Cancer Trials Collaborative Group, 1992, "Systemic treatment of early breast cancer by hormonal, cytotoxic, or immune therapy" *Lancet* 339(8785):71-85.

Osborne CK et al., 1991, "Acquired Tamoxifen Resistance: Correlation With Reduced Breast Tumor Levels of Tamoxifen and Isomerization of Trans-4-Hydroxytamoxifen", *J Natl Cancer Inst.* 83(20):1477-1482.

Saez R et al., 1989, Hormonal Treatment of Advanced Breast Cancer *Hormone Therapy of Breast Cancer,* pp. 163-172.

Osborne CK et al., 1987, "Human Breast Cancer in the Athymic Nude Mouse: Cytostatic Effects of Long-term Antiestrogen Therapy" *Eur J Cancer Clin Oncol.* 23(8):1189-1196.

Hoogstraten B et al., 1984, Combined Modality Therapy for First Recurrence of Breast Cancer *Cancer* 54(10):2248-2256.

Pritchard KI et al., 1980, "Tamoxifen Therapy in Premenopausal Patients With Metastatic Breast Cancer" *Cancer Treat Rep.* 64(6-7):787-96.

Rabenoelina F et al., 2002, "Effect of prolonged hydroxytamoxifen treatment of MCF-7 cells on mitogen activated kinase cascade" *Int J Cancer* 98(5):698-706.

Alsayed Y et al., 2001, "Activation of Rac1 and the p38 mitogen-activated protein kinase pathway in response to all-trans-retinoic acid" *J Biol Chem* 276(6):4012-4019.

NCBI Accession No. AF012108; Aug. 19, 1997; *Homo sapiens* Amplified in Breast Cancer (AIBI) mRNA, Complete CDs; Last Accesses 5/25/206; www.ncbi.nlm.nih.gov; pp. 4.

NCBI Accession No. BD192354; Jul. 17, 2003; AIB1, A Steroid Receptor Co-Activator; Last Accessed May 25, 2006; www.ncbi.nlm.nih.gov; pp. 3.

NCBI Accession No. AAC51677; Aug. 13, 1997; Amplified in Breast Cancer [*Homo Sapiens*]; Last Accessed May 25, 2006; www.ncbi.nlm.nih.gov; pp. 2.

Anzick et al.; "AIB1, a steroid receptor coactivator amplified in breast and ovarian cancer"; Science, vol. 277; pp. 965-968, Aug. 15, 1997.

NCBI Accession No. NP_001871; Mar. 19, 1999; cAMP Responsive Element Binding Protein 2 [*Homo sapiens*]; Last Accessed May 25, 2006; www.ncbi.nlm.nih.gov; pp. 2.

NCBI Accession No. NM_001880; Mar. 19, 1999; *Homo Sapiens* cAMP Responsive Element Binding Protein 2 (CREB2) mRNA; Last Accessed May 25, 2006; www.ncbi.nlm.nih.gov; pp. 2.

Maekawa et al.; "Leucine zipper structure of the protein CRE-BP1 binding to the cyclic AMP response element in brain"; *EMBO J.*, vol. 8, No. 7; pp. 2023-2028, 1989.

NCBI Accession No. S40706; Sep. 28, 1992; GADD153 growth arrest and DNA-damage-inducible gene[human, Genomic/mRNA, 895 nt]; Last Accessed May 25, 2006; www.ncbi.nlm.nih.gov; pp. 2.

NCBI Accession No. S40706; Sep. 28, 1992; Gadd153 [human, Peptide, 168 aa]; Last Accessed May 25, 2006; ; www.ncbi.nlm.nih.gov; pp. 2.

NCBI Accession No. CR542252; Jun. 29, 2004; *Homo sapiens* full open reading frame cDNA clone RZPDo834C0626D for gene ELK1, ELK1, member of ETS oncogene family,; complete cds, incl. stopcodon; Last Accessed May 25, 2006; www.ncbi.nlm.nih.gov; pp. 3.

NCBI Accession No. CAG47048; Jun. 29, 2004; ELK1 [*Homo sapiens*]; Last Accessed May 25, 2006; www.ncbi.nlm.nih.gov; pp. 2.

NCBI Accession No. NM_000125; Mar. 19, 1999; *Homo sapiens* estrogen receptor 1 (ESR1) mRNA; Last Accessed May 25, 2006; www.ncbi.nlm.nih.gov; pp. 5.

NCBI Accession No. NP_000116; Mar. 19, 1999; Estrogen receptor 1 [*Homo sapiens*]; Last Accessed May 25, 2006; www.ncbi.nlm.nih.gov; pp. 4.

Mosselman et al:; "ERβ: Identification and Characterization of a Novel Human Estrogen Receptor"; *FEBS Letters,* vol. 392; pp. 49-53, 1996.

NCBI Accession No. NM_001437; Oct. 17, 2000; *Homo sapiens* estrogen receptor 2 (ER beta) (ESR2), mRNA; Last Accessed May 25, 2006; www.ncbi.nlm.nih.gov; pp. 2.

NCBI Accession No. NP_001428; Oct. 17, 2000; Estrogen receptor 2 (ER beta) [*Homo sapiens*]; Last Accessed May 25, 2006; www.ncbi.nlm.nih.gov; pp. 2.

NCBI Accession No. X68505; Oct. 13, 1992; *H. sapiens* mRNA for myocyte-specific enhancer factor 2 (MEF2); Last Accessed May 25, 2006; www.ncbi.nlm.nih.gov; pp. 3.

NCBI Accession No. X68505; Oct. 13, 1992; Myocyte-specific enhancer factor 2 (MEF2); Last Accessed May 25, 2006; www.ncbi.nlm.nih.gov; pp. 2.

NCBI Accession No. P49137; Feb. 1, 1996; MAP Kinase-Activated Protein Kinase 2 (MAPK-Activited Protein Kinase 2) (MAPKAP Kinase 2) (MAPKAPK-2);Last Accessed May 25, 2006; www.ncbi.nlm.nih.gov; pp. 3.

Waskiewicz et al.; "Mitogen-activated protein kinase activated the serine/threonine kinases Mnk1 and Mnk2" ; *EMBO J.*, vol. 16, No. 8; pp. 1909-1920, 1997.

Deak et al.; "Mitogen- and stress-activated protein kinase-1 (MSK1) is directly activated by MAPK and SAPK2/p38, and may mediate activation of CREB"; *EMBO J.*, vol. 17, No. 15; pp. 4426-4441, 1998.

NCBI Accession No. AF074393; Aug. 10, 1998; *Homo sapiens* nuclear mitogen- and stress-activated protein kinase-1 (MSK1) mRNA; complete cds; Last Accessed May 25, 2006; www.ncbi.nlm.nih.gov; pp. 3.

NCBI Accession No. AAC31171; Aug. 10, 1998; Nuclear mitogen- and stress-activated protein kinase-1 [*Homo sapiens*]; Last Accessed May 25, 2006; www.ncbi.nlm.nih.gov; pp. 2.

Lee et al.; "A protein kinase involved in the regulation of inflammatory cytokine biosynthesis"; *Nature*, vol. 372; pp. 739-746, 1994.

NCBI Accession No. L35263; Dec. 22, 1994; Human CSaids binding protein (CSBP1) mRNA, complete cds; Last Accessed May 25, 2006; www.ncbi.nlm.nih.gov; pp. 3.

NCBI Accession No. Q16539; Feb. 1, 1997; Mitogen-Activated Protein Kinase p38 (MAP Kinase p38) (Cytokine Suppressive Anti-Inflammatory Drug Binding Protein) (CSaid Binding Protein) (CSBP) (Max-Interacting Protein 2) (MAP kinase MX12); Last Accessed May 25, 2006; www.ncbi.nlm.nih.gov; pp. 3.

Jiang et al.; "Characterization of the structure and function of a new mitogen-activated protein kinase (p38β)"; *J. Biol. Chem.*, vol. 271, No. 30; pp. 17920-17926, Jul. 26, 1996.

NCBI Accession No. NM_139014; May 20, 2002; *Homo sapiens* mitogen-activated protein kinase 14 (MAPK14), transcript variant 4, mRNA; Last Accessed May 25, 2006; www.ncbi.nlm.nih.gov; pp. 5.

NCBI Accession No. U53442; Jul. 30, 1996; Human p38Beta MAP kinase mRNA, complete cds; Last Accessed May 25, 2006; www.ncbi.nlm.nih.gov; pp. 2.

Jiang et al.; Characterization of the structure and function of the fourth member of p38 group mitogen-activated protein kinases, p38δ; *J. Biol. Chem.*, vol. 272, No. 48; pp. 30122-30128, Nov. 28, 1997.

NCBI Accession No. NP_620583; May 20, 2002; Mitogen-activated protein kinase 14, isoform 4; cytokine suppressive anti-inflammatory drug binding protein; Csaids binding protein; MAP kinase Mxi2; p38 mitogen activated kinase; p38 MAP kinase; p38alpha Exip; stress-activated protein kinase 2A; MAX-interacting protein 2 {*Homo sapiens*]; Last Accessed May 25, 2006; www.ncbi.nlm.nih.gov; pp. 4.

Wang et al.; "Molecular cloning and characterization of a novel p38 mitogen-activated protein kinase"; *J. Biol. Chem.*, vol. 272, No. 38; pp. 23668-23674, Sep. 19, 1997.

NCBI Accession No. AF015256; Sep. 8, 1997; *Homo sapiens* p38 mitogen-activated protein kinase (p38 delta) mRNA, complete cds; Last Accessed May 25, 2006; www.ncbi.nlm.nih.gov; pp. 2.

NCBI Accession No. AF015256; Aug. 22, 1997; p38 mitogen-activated protein kinase [*Homo sapiens*]; Last Accessed May 25, 2006; www.ncbi.nlm.nih.gov; pp. 2.

NCBI Accession No. X79483; Jun. 6, 1996; *Homo sapiens* ERK5 mRNA for extracellular signal regulated kinase; Last Accessed May 25, 2006; www.ncbi.nlm.nih.gov; pp. 2.

NCBI Accession No. X79483.8; Jun. 6, 1996; Extracellular signal regulated kinase; Last Accessed May 25, 2006; www.ncbi.nlm.nih.gov; pp. 2.

Lechner et al.; "ERK6, a mitogen-activated protein kinase involved in C2C12 myoblast differentiation"; *Proc. Natl. Acad. Sci. USA*, vol. 93; pp. 4355-4359, 1996.

New et al.; "PRAK, a novel protein kinase regulated by the p38 MAP kinase"; *EMBO J.*, vol. 17, No. 12; pp. 3372-3384, 1998.

NCBI Accession No. AF032437; May 16, 1998; *Homo sapiens* mitogen-activated protein kinase activated protein kinase gene, complete cds; Last Accessed May 25, 2006; www.ncbi.nlm.nih.gov; pp. 2.

NCBI Accession No. NP_620777; May 28, 2002; Mitogen-activated protein kinase-activated protein kinase 5, isoform 2, p38-regulated/activated protein kinase [*Homo sapien*]; Last Accessed May 25, 2006; www.ncbi.nlm.nih.gov; pp. 3.

Pierrat et al.; "RSK-B, a novel ribosomal S6 kinase family member, is a CREB kinase under dominant control of p38α mitogen-activated protein dinase (p38α MAPK)"; *J. Biol. Chem.*, vol. 273, No. 45; pp. 29661-29671, 1998.

NCBI Accession No. NM_003942; Mar. 19, 1999; *Homo sapiens* ribosomal protein S6 kinase, 90kD, polypeptide 4 (RPS6KA4) mRNA; Last Accessed May 25, 2006; www.ncbi.nlm.nih.gov; pp. 3.

NCBI Accession No. AJ010119; Aug. 25, 1998; Ribosomal protein kinase B (RSK-B) [*Homo sapiens*]; Last Accessed May 25, 2006; www.ncbi.nlm.nih.gov; pp. 2.

NCBI Accession No. AAW56072; Jan. 19, 2005; Signal Transducer and activator of transcription 1, 91kDa [*Homo sapiens*]; Last Accessed May 25, 2006; www.ncbi.nlm.nih.gov; pp. 2.

NCBI Accession No. AY865620; Jan. 19, 2005; *Homo sapiens* signal transducer and activator of Transcription 1, 91kDa (STAT1) gene, complete cds; Last Accessed May 25, 2006; www.ncbi.nlm.nih.gov; pp. 32.

Wu et al., Selective Phosphorylations of the SRC-3/AIB1 Coactivator Integrate Genomic Reponses to Multiple Cellular Signaling Pathways, *Mol. Cell*, 15:937-949, Sep. 24, 2004.

* cited by examiner

P38 MAPK PATHWAY PREDICTS ENDOCRINE-RESISTANT GROWTH OF HUMAN BREAST CANCER AND PROVIDES A NOVEL DIAGNOSTIC AND TREATMENT TARGET

This application claims the benefit of U.S. Provisional Application Ser. No. 60/299,824 filed on Jun. 21, 2001.

This work was supported by a grant from the National Institutes of Health/National Cancer Institute grant number P50 CA58183. Accordingly, the government has certain rights in the invention.

BACKGROUND OF THE INVENTION

Breast cancer development and progression are influenced by steroid hormones, particularly estrogen, via their interaction with specific target cell receptors. Tamoxifen is a non-steroidal antiestrogen which is now the most frequently used drug in breast cancer treatment. Tamoxifen is thought to inhibit breast cancer growth by competitively blocking estrogen receptor (ER), thereby inhibiting estrogen-induced growth. ER, a ligand-dependent transcription factor, meditates most biological effects of estrogens on cell and tumor growth [Katzenellenbogen et al., 2000, *Recent Prog Norm Res* 55:163–195]. In the adjuvant setting after primary surgery for breast cancer, tamoxifen has been shown to prolong disease-free and overall survival, and it has also been shown to induce remissions in more than half of patients with metastatic disease who have ER-positive tumors [Early Breast Cancer Trials Collaborative Group, 1992, *Lancet* 339:1–14, 71–85; Saez et al., 1989, *Current Clinical Oncology*, Alan R Liss Inc., New York, pp. 163–172]. Although tamoxifen is initially effective in many patients, 50% of the patients fail to respond to the drug despite the presence of ER. Furthermore, even patients who initially respond eventually acquire tamoxifen resistance, leading to tumor progression and death. The mechanisms for either intrinsic or acquired tamoxifen resistance are unknown, but they are probably multifactorial.

In both animal models and clinical specimens, lower tamoxifen uptake and somewhat altered tamoxifen metabolism in resistant tumors have been observed, but neither appears to explain tamoxifen stimulation of the resistant tumors. Nor do estrogen receptor losses or mutations appear to explain this phenomenon, although altered expression of transcriptional variant forms of the receptor may well contribute. Pure steroidal antiestrogens such as ICI 182,780 are capable of reversing tamoxifen-stimulated as well as estrogen-stimulated growth of these resistant tumors, and are now in clinical trials for this purpose [Osborne et al., 1994, *Breast Cancer Res Treat.* 32(1):49–55]. Endocrine treatment of breast cancer is the major form of systemic adjuvant therapy and therapy for metastatic disease. Unfortunately, however, not all tumors will respond, and furthermore, initially responding tumors eventually become resistant to the endocrine treatment, leading to tumor progression and death.

The present inventors are interested in the mechanisms by which tumors develop resistance to tamoxifen, with the ultimate goal of developing new strategies for preventing or reversing the emergence of resistant cells. There are several possible mechanism by which tamoxifen resistance could develop in breast cancer cells. Clues to these mechanisms can be gleaned from an understanding of the myriad effects that tamoxifen has at the cellular level, as outlined in FIG. 1. Tamoxifen binds to the ER and competitively blocks estrogen-induced transcription of specific genes encoding proteins involved with regulation of cell proliferation. Some of these proteins are in fact polypeptide growth factors, such as transforming growth factor α, insulin-like growth factor II, and members of the fibroblast growth factor family, which by autocrine and paracrine mechanisms may enhance tumor growth. Down-regulation of the gene expression of these growth factors by tamoxifen may result in suppression of tumor growth. Oddly enough, breast cancer cells, as well as other tumor cells, may also synthesize and secrete growth inhibitors, such as transforming growth factor-β. Expression of TGFβ is reduced by estrogen, but enhanced by tamoxifen treatment. Thus, increased expression of growth inhibitors by tamoxifen may also contribute to tumor growth suppression. Clearly, alterations in the expression of these growth factors or growth inhibitors, or their specific cell membrane receptors, could provide the tumor cell with sufficient growth stimulation to overcome the tamoxifen block, resulting in tamoxifen resistance. Cross-talk between polypeptide growth factor pathways and ER-mediated events could also theoretically result in tamoxifen resistance. It has been shown, for example, that increasing the level of cellular cyclic AMP pharmacologically alters the cellular response to tamoxifen, converting it from an antiestrogen to a weak estrogen agonist [Fujimoto et al., 1994, *Mol Endocrinol.* 8(3):296–304]. The mechanism for this phenomenon is not yet understood, but it could be related to changes in the phosphorylation state of the ER itself and/or its coregulatory protein.

Other potential mechanisms for the development of tamoxifen resistance include the loss of or mutations in the ER, or altered expression of the accessory proteins that could modify the transcriptional signal generated by the ligands binding to estrogen receptor. Also, since certain metabolites of tamoxifen are known to be less antiestrogenic, or even to be full estrogen agonists, changed systemic metabolism of tamoxifen or altered uptake or metabolism of tamoxifen in the tumor itself could also result in tamoxifen resistance. Finally, high levels of the so-called antiestrogen binding sites, cytoplasmic binding sites whose function is not yet well understood, could theoretically serve as a sump, soaking up tamoxifen molecules and preventing their binding to ER. Studies of several of these possibilities have been initiated in laboratory models.

Clinical studies with tamoxifen provide several clues for mechanisms by which acquired resistance may develop. Patients whose tumors initially lack ER have a very low response rate to the drug, and thus, selection of an ER-negative clone of tumor cells could result in an estrogen-independent tumor refractory to tamoxifen. Some patients with tamoxifen resistance do develop resistance to all forms of endocrine therapy via selection of an ER-negative tumor cell clone. However, it was recently reported that a series of patients with acquired tamoxifen resistance in whom tumor estrogen and progesterone receptors were measured by both ligand binding and immunohistochemical assays (to circumvent the problem of receptor occupancy by the drug) [Encarnacion et al., 1993, *Breast Cancer Res. Treat.* 26(3):237–246]. More than 60% of tumors continued to express ER and/or PgR even while progressing in the face of tamoxifen. These data indicate that while ER negativity may account for some cases of resistance, mechanisms of resistance other than receptor loss must be common.

If patients' tumors remain ER-positive after development of tamoxifen resistance, one might expect that some of these tumors have retained estrogen sensitivity and will respond to other endocrine treatments. In fact, clinical experience demonstrates that patients who have initially responded to tamoxifen but who later develop tumor progression, frequently respond to second or third-line endocrine therapies. Thus, acquired tamoxifen resistance in these patients does not necessarily indicate global hormonal unresponsiveness, but rather selective resistance to tamoxifen itself. Although it has not been studied systematically, anecdotal experience suggests that some patients with tamoxifen resistance will respond to a rechallenge with the drug after an interval in which they receive other treatments. Furthermore, clinical reports suggest that patients who receive tamoxifen adjuvant therapy and then later recur, not infrequently will respond to a rechallenge with the drug. This suggests that tamoxifen resistance, in some cases, may not be a permanent phenotype, but rather may be reversible when administration of the drug is stopped. Patients may also respond to an increase in the tamoxifen dose after developing progression with a lower dose schedule. Finally, similar to reports of patients treated with high dose estrogen therapy, some patients who have responded to tamoxifen will have a withdrawal response when the drug is stopped at the time of tumor progression. The prolonged half-life of tamoxifen makes it difficult for clinicians to withhold alternative therapy while waiting for a withdrawal response to the drug. Nevertheless, these data strongly suggest that in some patients with acquired resistance, tamoxifen may actually be stimulating tumor growth.

Two previously published clinical trials also suggest that tamoxifen-stimulated tumor growth may be a cause of tamoxifen resistance in some patients [Pritchard et al., 1980, *Cancer Treat Rep.* 64(6–7):787–96][Hoogstraten et al., 1984, *Cancer* 54(10):2248–2256]. In these studies, premenopausal women with advanced breast cancer were treated with second-line ovarian ablation after they first responded and then progressed on tamoxifen. In one of these studies, the secondary response to ovarian ablation was common in patients who had previously responded to tamoxifen, suggesting that tamoxifen treatment served as an in vivo tumor estrogen sensitivity assay. However, in the other study, opposite results were obtained and no patients responded to second-line ovarian ablation. In this latter study tamoxifen therapy was continued after the surgery, while in the first study tamoxifen treatment was stopped. Secondary response to ovarian ablation would not be expected in the latter study if tamoxifen itself was behaving as an estrogen agonist and stimulating tumor growth. Tamoxifen-stimulated tumor growth as a mechanism for acquired resistance is further supported by data from the present inventor's laboratory as well as others using experimental models. A major focus of the present inventor's group is to better understand mechanisms by which tamoxifen-stimulated tumor growth occurs.

SUMMARY OF THE INVENTION

Endocrine treatment of breast cancer is the major form of systemic adjuvant therapy and therapy for metastatic disease. Unfortunately not all tumors respond, and furthermore, initially responding tumors eventually become resistant to endocrine therapies [Osborne, 1998, *N Engl J Med* 339: 1609–1618]. This may lead to tumor progression and death. Identifying the factors and pathways responsible for the development of this resistance and defining ways to overcome this resistance are, therefore, important diagnostic and therapeutic goals in breast cancer research.

The present invention provides a method of predicting resistance to endocrine treatment comprising providing a biological sample, e.g. a breast tumor biopsy, and detecting the activity and/or expression of p38 MAPK and/or AIB1.

The present invention further provides a method for treating breast cancer comprising contacting a breast tumor with a p38 MAPK inhibitor. The p38 MAPK inhibitor may be administered to a subject and may be combined with an endocrine therapy. Administration of the p38 MAPK inhibitor may ameliorate, reverse or prevent endocrine resistance. Thus, the present invention provides a method of ameliorating or reversing de novo endocrine resistance and a method of ameliorating, reversing or preventing acquired endocrine-resistance in an endocrine-resistant tumor.

The present invention further provides a method of treating a breast cancer comprising contacting a breast tumor with an inhibitor of the p38 MAPK pathway including inhibitors that act upstream or downstream of p38 MAPK.

Use of the therapeutic methods of the invention should improve survival of breast cancer patients.

The invention further relates to drug screening assays designed to identify compounds that modulate p38 MAPK activity and the use of such compounds in the treatment of disorders such as cancer. The invention also relates to methods for diagnosis and prognosis of disorders such as cancer that rely on detection of activation or overexpression of p38 MAPK. In one preferred embodiment, the invention relates to methods for diagnosis an prognosis of breast cancer and/or prostrate cancer.

The invention is supported by the discovery that p38 MAPK is up-regulated when breast tumors develop resistance to the endocrine treatments such as estrogen withdrawal or tamoxifen. Up-regulation of p38 MAPK has been observed in an athymic mouse xenograft model of endocrine resistance (e.g. Example 2, below) and in a survey of over 150 biopsies of tamoxifen resistant breast tumors. This invention is further supported by the discovery that p38 MAPK is upregulated in breast tumors that display de novo tamoxifen resistance.

Thus, patient tissue may be assayed for levels of p38 MAPK activity or expression, wherein increased levels of p38 MAPK activity or expression signify an increased likelihood of resistance to endocrine treatments. In addition, the assays of the invention may be used to monitor the progression of the disease within a patient.

The invention further relates to assays designed to screen for compounds that modulate the biological activity of p38 MAPK (e.g. catalytic activity) or genes and gene products upstream or downstream to p38 MAPK. The invention also relates to assays designed to screen for compounds that modulate p38 MAPK gene expression. For example, cell-based assays may be used to screen for compounds that modulate p38 MAPK transcription such as compounds that modulate expression, production or activity of transcription factors involved in p38 MAPK gene expression; antisense and ribozyme polynucleotides that modulate translation of p38 MAPK mRNA and polynucleotides that form triple helical structures with the p38 MAPK regulatory region and inhibit transcription of the p38 MAPK gene.

Identified compounds may be used in the treatment of disorders such as cancer including breast and ovarian cancer where activity or transcription of p38 MAPK contributes to tumor development or growth or resistance to therapy.

The invention also provides p38 MAPK inhibitors and p38 MAPK pathway inhibitors that may be used to ameliorate or prevent de novo or acquired estrogen resistance. In some embodiments of the invention, the amount of a p38 MAPK inhibitor administered to a subject is from about 1 mg/kg to about 100 mg/kg. In some embodiments, the amount is from about 5 mg/kg to about 60 mg/kg. In some embodiments administration of a p38 MAPK inhibitor is coextensive with administration of an endocrine agent. In other embodiments of the invention, p38 MAPK inhibitor administration begins before or after endocrine administration begins.

Inhibitors of the invention may be small organic molecules, antibodies, or nucleic acids that inhibit the biological activity of a member of the p38 MAPK pathway. Inhibition may be accomplished by any means including reducing catalytic activity (e.g. small molecule inhibitors), reducing protein availability (e.g. antibodies), reducing gene product formation (e.g. antisense nucleic acids), and increasing gene product turnover (e.g. dephosphorylation, ubiquitination).

DETAILED DESCRIPTION OF THE INVENTION

Figure 1:
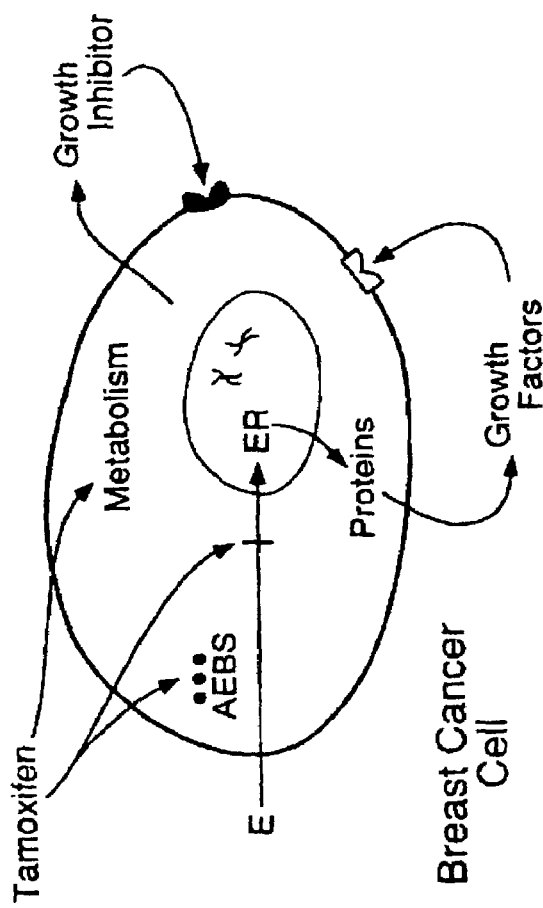
FIG. 1: Schematic diagram of the mechanism of tamoxifen action.

According to the instant invention, the term "endocrine therapy" means any therapy designed to interrupt the signal generated by estrogen binding to estrogen receptor. Nonlimiting examples include treatments which lower the estrogen level and treatments designed to block the estrogen receptor such as administration of the drug tamoxifen.

According to the instant invention, the term "estrogen withdrawal" means any therapy designed to reduce the level of estrogen in a subject. Estrogen withdrawal may be accomplished by ovarian ablation or surgical removal. Estrogen withdrawal also may be accomplished by administering to the subject a molecule that inhibits estrogen formation or enhances estrogen degradation. Estrogen withdrawal also may be accomplished by administering to the subject a molecule that converts estrogen to an inactive form.

According to the instant invention, the term "p38 MAPK inhibitor" means any material that blocks signaling through the p38 MAP kinase pathway. In some embodiments of the invention, p38 MAPK inhibitors function by reducing the amount of p38 MAPK, inhibiting or blocking p38 MAPK activation, or inhibiting other molecules in the signaling pathway.

Non-limiting examples of p38 MAPK inhibitors include antisense p38 MAPK nucleic acids and fragments thereof. Further non-limiting examples of p38 MAPK inhibitors include antibodies that bind p38 MAPK and fragments thereof. Still further non-limiting examples of p38 MAPK inhibitors include EO-1428, PD169316, SB202190, SB203580, SB239063 (Legos et al., 2001, Brain Res. 892: 70–77; Barone et al., 2001, Med Res Rev. 21(2):129–145), SB281832, VX-702, VX-745, ZM336372, RPR 200765A (Mclay LM et al., 2001, Bioorg Med Chem. 9(2):537–554), and N-(3-tert-butyl-1-methyl-5-pyrazolyl)-N'-(4-(4-pyridinylmethyl)phenyl)urea (Dumas J, 2002, Bioorg Med Chem Lett 12(12):1559–62).

According to the instant invention, the term "p38 MAPK activity" means the ability of p38 MAPK to phosphorylate, inter alia, amplified in breast cancer 1 (AIB 1), activating transcription factor 2 (ATF-2), estrogen receptor α (ERα), estrogen receptor β (ERβ), mitogen activated protein kinase activated protein kinase 2 (MAPKAP-K2), MAPKAP-K3, p38-related/activated protein kinase (PRAK), Menkes copper transporting P-type ATPase (MNK), mitogen- and stress-activated protein kinase (MSK), ribosomal S6 kinase B (RSK-B), signal transducer and activator of transcription 1 (STAT1), Max/Myc complex, Ets-like transcription factor-1 (Elk1), C/EBP homologous protein (CHOP), myocyte enhancer factor 2 (MEF2), and fragments thereof as measured by any phosphorylation assay known in the art. Nonlimiting examples of phosphorylation assays include activity assays (e.g. in-gel kinase assays) and immunologic assays (e.g. use of an antibody that specifically binds to the phosphorylated protein in immunohistochemistry, immunofluorescence, Western blotting, and ELISA).

According to the instant invention, the term "p38 MAPK expression" means the formation of a p38 MAPK gene product as measured by any method known in the art including nucleic acid hybridization method, e.g. Northern blotting, in situ hybridization; nuclear run-on assays; polymerase chain reaction amplification; reporter gene expression, i.e. where the reporter gene is operatively linked to p38 MAPK expression control sequences; gene expression arrays. Formation of a p38 MAPK gene product may also be measured by any antibody-based technique including immunohistochemistry, immunofluorescence, Western blotting, and ELISA.

According to the instant invention, the term "providing a biological sample" means supplying cells, fluids, tissues and/or organs by any means such that said cells, fluids, tissues, and/or organs are suitable for p38 MAPK pathway activity and/or expression analysis. In some embodiments of the invention, the biological sample is biopsied, resected, drawn or otherwise harvested from a subject. In other embodiments of the invention, the biological sample is presented for analysis within its native in vivo context. A nonlimiting example is novel magnetic resonance imaging (Jacobs et al., 2001, J Nucl Med 42(3):467–475; Wunderbaldinger et al., 2000, Eur J Radiol 34(3):156–165) techniques wherein the biological sample may be identified and subjected to p38 MAPK pathway activity and/or expression analysis while remaining in a living subject throughout. Expression of p38 MAPK pathway genes may be detected using a nucleic acid construct comprising a p38 MAPK pathway gene expression control sequence operatively linked to a reporter gene. This nucleic acid may be delivered to cells in vitro or in vivo using particle bombardment [U.S. Pat. No. 5,836,905 to Lemelson et al.] or any other delivery technique known in the art.

According to the instant invention, the term "resistance", i.e. endocrine resistance, estrogen withdrawal resistance or tamoxifen resistance means that a tumor does not regress (get smaller) or have prolonged stable disease (no change in size) when a new treatment is initiated. In other words the tumor maintains its exact size for a minimum of 6 months, a condition called stable disease, or it regresses by more than 50% in volume, which is a response. Tumors that do not qualify for either one of these are de novo resistant to the treatment. For acquired resistance, tumors initially regress and get smaller, but then as they become resistant the begin to regrow. The standard definition is that the tumor volume increases by 25%. This indicates that the treatment is no longer working and another therapy must be substituted. Thus, resistance is a clinical term used to indicate that the that the treatment is not working because the tumor is progressing. De novo resistance can usually be detected within the first 4 to 8 weeks of treatment. If the tumor is going to respond to the treatment then it will usually stop growing or actually regress by this time. For acquired resistance the tumor remains stable or regresses in size for a minimum of size months in order for it to be called a response. The indicator of the development of acquired resistance is when the tumor progresses after this period of response and begins to regrow.

Current endocrine therapies of breast cancer are based mainly on targeting the estrogen receptor (ER) signaling pathway by either reducing levels of estrogen or by antagonizing ER function with antiestrogens such as Tam. There are numerous prognostic markers in breast cancer, but there are few biological markers which predict response to treatment. Furthermore, though ER status itself is a vital factor and therefore a predictor of response to hormone therapy, it nevertheless fails to predict the de novo and acquired resistance that occurs in a significant portion of ER-positive patients. It is known that different growth factor pathways and their downstream MAPKs can modulate endocrine response. However, the underlying molecular events that contribute to endocrine resistance of breast cancer are yet unknown. Identifying the factors and pathways responsible for the development of this resistance and defining ways to overcome this resistance are, therefore, important diagnostic and therapeutic goals in breast cancer management.

Therefore, what is unique about the present inventor's discovery is that the p38 MAPK pathway, which has been implicated in inflammation and cellular stress, predicts response to endocrine treatment in breast cancer; specifically, its activation and/or increased expression is associated with the development of resistance to common treatments in breast cancer, namely antiestrogens and estrogen withdrawal. The clinical implication is that endocrine-resistant tumor growth might be prevented with inhibitors of p38 MAPK (or other proteins in this pathway) used simultaneously with the endocrine treatment or added later at the first sign of tumor resistance. Measurements of expression and/or activity of p38 MAPKs (or other proteins on this pathway) might also serve as diagnostic markers to select patients for endocrine therapy.

While the literature has suggested that ERK 1,2 MAPK, as well as other MAPK pathways, are able to phosphorylate and modulate activity of the ER [Kato et al., 1995, Science 270(5241):1491–1494], the association of acquired breast cancer endocrine resistance with the up-regulation of the p38 MAPK pathway is disclosed for the first time by the instant invention.

Various aspects of the invention may be better understood in view of the following detailed descriptions, example, and supporting references.

EXAMPLES

Example 1

The present inventors have developed an in vivo experimental model of tamoxifen resistance and resistance to estrogen deprivation in which ER-positive MCF-7 human breast cancer cells are inoculated subcutaneously into athymic nude mice [Osborne et al., 1987, *Eur J Cancer Clin Oncol.* 23(8):1189–1196; Osborne et al., 1991, *J Natl Cancer Inst.* 83(20):1477–1482]. Estrogen withdrawal (-E2) or tamoxifen treatment of these mice suppresses tumor growth for several months, but then tumor growth resumes despite continued treatment with the drug [Osborne et al., 1995, *J Natl Cancer Inst* 87:746–750]. This sequence of events is similar to that which occurs in patients. Transplantation of fragments from these tamoxifen-resistant tumors demonstrates that their growth has not become estrogen-independent, but in fact is now stimulated by tamoxifen as well as by estrogen. These data, which have also been reported by others [Katzenellenbogen et al., 2000, *Recent Prog Norm Res* 55:163–195], suggest that one form of acquired tamoxifen resistance may be due to the acquired ability of the tumor cells to be stimulated rather than inhibited by tamoxifen. Since certain metabolites of tamoxifen have estrogenic properties, pharmacologic explanations for this tamoxifen-stimulated growth were investigated first.

Conversion of breast tumors to a (tamoxifen-resistant) $Tam^R$ phenotype, and to lesser extent to (estrogen-deprived-resistant) $-E2^R$, has been shown to be associated with oxidative stress and marked depletion of glutathione levels [Schiff et al., 2000, *J Natl Cancer Inst* 92:1926–1934]. These cellular events may induce stress-induced signaling pathways which could be important in mediating cell proliferation and resuming breast tumor growth. And indeed, in a xenograft model $-E2^R$ and $Tam^R$ resistance have recently been shown to be associated with increased levels of the phosphorylated active form of p38 MAPK, a stress-induced kinase. Importantly also, these resistant tumors have been found to possess high levels of ER and, in addition, that the $-E2^R$ tumors are hypersensitive to low levels of estrogen. Also, it has been shown that $-E2^R$ and $Tam^R$ resistant tumors can still be inhibited by the pure steroidal antiestrogen ICI 182,780 which induces ER degradation and depletion from the cell [Osborne et al., 1995, *J Natl Cancer Inst* 87:746–750]. These findings argue that the resistant-growth of these tumors is mediated through the ER, but that the ER activity has been modulated. ER phosphorylation, which leads to enhancement in receptor activity [Wolgel, 1996, *Biochem J* 319:657–667], is one possible mechanism. Based on the above results, increased activity of p38 MAPK may be an important determinant in the development of endocrine resistance of breast tumors, presumably through direct phosphorylation of ERα, ERβ, and AIB1. Hence, p38 MAPK may serve as a therapeutic target to circumvent endocrine resistance of breast cancer. This is further supported by a recent report which suggested the involvement of p38 MAPK in mediating MEKK1-induced activation of the human ERα and in stimulating the agonistic activity of Tam in endometrial and ovarian cancer cells [Lee et al., 2000, *Mol Endocrinal* 14:1882–1896]. Importantly also, the inventor's data suggests that p38 MAPK can phosphorylate ERα and ERβ in vitro and that the AF-1 and hinge domains of the ERα receptor may be involved.

Example 2

Methods

ER-positive MCF-7 human breast cancer cells were grown as xenografts in athymic nude mice as described previously [Osborne et al., 1987, Eur J Cancer Clin Oncol. 23(8): 1189–1196; Osborne et al., 1991, J Natl Cancer Inst. 83(20):1477–1482; Osborne et al., 1995, J Natl Cancer Inst 87:746–750]. Day 0 was the day of transplantation conducted and the day estrogen treatment began. These mice were treated with estrogen withdrawal (-E2) or tamoxifen (Tam) beginning on day 17. Tumor volume was measure every four days.

Western blots were performed using an antibody that recognizes only the phosphorylated (active) form of p38 MAPK. Tumor fine powder was homogenized on dry ice with lysis buffer (20 mM Tris-HCl (pH 7.5), 150 mM NaCl, 1 mM $Na_2EDTA$, 1 mM EGTA, 1% Triton, 2.5 mM sodium pyrophosphate, 1 mM beta-glycerophosphate, 1 mM $Na_3VO_4$, 1 µg/mL leupeptin, 10% Glycerol, 1 mM Pherryl Methylsulfonyl Fluoride, 0.12 mg/mL Antipain-HCl, 0.02 mg/mL Bestatin, 0.04 mg/mL Chrymostatin, 0.12 mg/mL E-64, 0.02 mg/mL Leupeptin, 0.02 mg/mL Pepstatin, 0.12 mg/mL Phosphor-amidon, 0.8 mg/mL pefabloc, 0.02 mg/mL Aprotinin, 1 µM Okadaic acid, 10 µg/mL Microsystin) at ratio 30 mg: 600 µL in pre-chilled glass homogenizer. Powder was then transferred to a prechilled Eppendorf tube. The extract was sonicated four times in 5-second bursts with 5-second intervals between bursts. The sonicated lysate was spun in a benchtop centrifuge at 13,000 rpm, 4° C. for 20 min. Clear lysate free of fat was transferred to a new prechilled tube and immediately stored at -80° C.

Aliquots of liquified lysate were subjected to Bradford assay (Bradford, 1976, Anal. Biochem. 72:248) to determine protein concentration.

Volumes of lysate sufficient to contain 20 µg each were heated to 95 to 100° C. for 5 min in buffer containing 62.5 mM Tris-HCl (pH 6.8 at 25° C.), 2% w/v SDS, 10% glycerol, 50 mM DTT, 0.01% w/v bromophenol blue. Denatured samples were subjected to standard SDS-PAGE and electrotransferred to a nitrocellulose membrane (0.2 µm, Millipore Inc.).

After transfer, each membrane was washed with 25 mL TBS (1 liter of 10×TBS: 24.2 g Tris base, 80 g NaCl; adjust pH to 7.6 with HCl) for 5 minutes at room temperature and incubated in 25 mL blocking buffer (1×TBS, 0.1% Tween-20 with 5% w/v nonfat dry milk). Blocking buffer (150 mL) was prepared by adding 15 mL of 10×TBA to 135 mL water, mixing, adding 7.5 g nonfat dry milk, mixing well, adding 0.15 mL Tween-20 (100%) while mixing, and continuing to mix for an additional hour at room temperature. Each membrane was then washed three times for 5 minutes each with 15 mL of TBS/T (1×TBS, 0.1% Tween-20).

Each membrane was then incubated in 10 mL primary antibody solution buffer (1×TBS, 0.1% Tween-20 with 5% nonfat dry milk) containing Phospho-p38 MAPK (Thr180/Tyr182) 28B10 Monoclonal Antibody (Cell Signaling Technology, Cat 9216) with gentle agitation overnight at 4° C. Following the overnight primary antibody incubation, each membrane was washed three times for 5 minutes each with 15 ml of TBS/T before incubating with HRP-conjugated secondary antibody (1:2000) and HRP-conjugated anti-biotin antibody (1:1000) to detect biotinylated protein markers in 10 ml of blocking buffer with gentle agitation for 1 hour at room temperature. Each membrane was washed three times for 5 minutes each with 15 ml of TBS/T following the secondary antibody incubation.

Membranes were then incubated with enhanced Chemiluminescent solution (Amershan Pharmacia), drained of excess developing solution, wrapped in plastic wrap and exposed to x-ray film.

Results

Estrogen withdrawal (-E2) or tamoxifen (Tam) treatment suppresses tumor growth for several months ($-E2^S$, $Tam^S$), but growth eventually resumes as the tumor become resistant to hormonal treatment ($-E2^R$, $Tam^R$). This is exemplified in FIG. 2A, wherein mice with wild type MCF-7 xenografts were treated with E2 withdrawal (Δ) or with Tam (□) and xenografted tumor volume is plotted as a function of time.

Acquired endocrine resistance is a major clinical problem in the management of breast cancer patients, but its mechanism is largely unknown.

Figure 2:
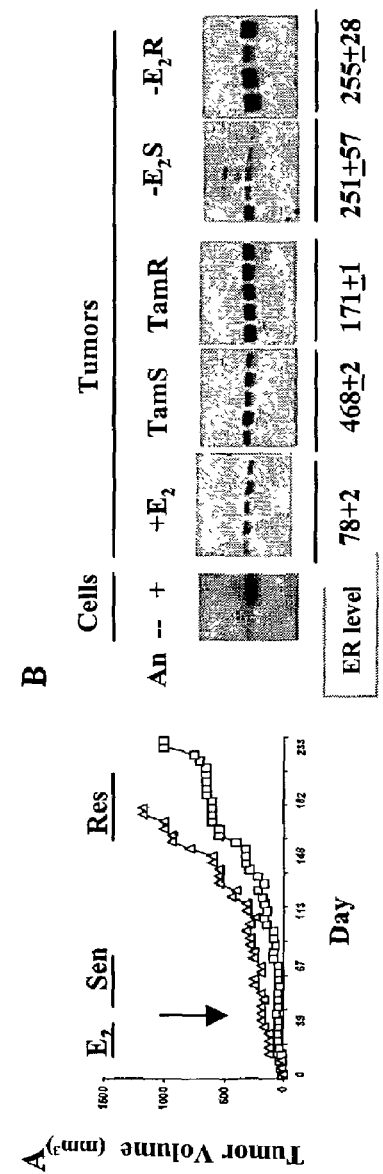
FIG. 2: Panel A shows the development of acquired resistance in xenografted tumors treated with E2 withdrawal (Δ) or with Tam (□). Panel B shows p38 MAPK activity as measured by Western blots using an antibody that recognizes the active (phosphorylated) form of p38. ER levels in tumors (fmol/mg protein) are shown.

In this model of endocrine resistance, p38 MAPK activity and estrogen receptor a (ERα) levels are up-regulated when breast tumors develop resistance to estrogen withdrawal (-E2) or Tamoxifen (Tam). Xenograft tumor extracts from control estrogen-treated (E2), Tam-sensitive ($Tam^S$), Tam-resistant ($Tam^R$), -E2-sensitive ($-E2^S$), and -E2-resistant ($-E2^R$) groups were analyzed with an antibody that recognizes the phosphorylated active form of p38 MAPK. Western blots using an antibody that recognizes only the phosphorylated (active) form of p38 MAPK are present in FIG. 2B. The left panel of FIG. 2B shows controls for phosphorylated p38 MAPK induction, wherein MCF-7 cells were left untreated (-) or treated in vitro (+) with 20 µg anisomycin (An) for 30 min., which is known to activate p38 MAPK (+control). The other five panels each consist of 4 or 5 lanes each loaded with a lance of a separate tumor. Active p38 MAP kinase increases in tumors developing resistance to E2 deprivation (-E2R) or tamoxifen (TamR) compared to the earlier sensitive phases (FIG. 2B). ER levels in the tumors (fmol/mg protein) are shown and remain high in the resistant tumors (FIG. 2B).

Example 3

It is also known that ER is subject to phosphorylation at several sites, and that this modification can cause ligand-independent and/or a synergistic increase in transcriptional activation of ER in the presence of estrogen and antiestrogen. Therefore, increased activity of p38 MAPK may be an important determinant in the development of endocrine resistance of breast tumors, presumably through direct phosphorylation of ERα that enhances the receptor activity in spite of reduced estrogen levels or treatment with antiestrogens such as Tam. Hence, p38 MAPK could serve as a clinical therapeutic target to delay, prevent, or reverse the development of resistance.

The instant invention provides an in vitro assay to show that p38 MAPK is capable of phosphorylating ER. Commercially available active recombinant p38 MAPK was used for this Example.

Reactions for Optimization 1 were set up with 1×kinase buffer (25 mM Tris-HCl (pH 7.5), 5 mM beta-glycerophosphate, 2 mM dithiothreitol (DTT), 0.1 mM $Na_3VO_4$, 10 mM $MgCl_2$) supplemented with various concentrations of cold ATP and a fixed amount of $\gamma$-$^{32}$P ATP (0.1 µCi, 1 µCi and 5 µCi per 20 µL of total volume, adenosine 5'-triphosphate, ICN Inc., Cat # 35001). These reactions further contained and a constant amount (0.5 µg per 20 µL of total volume) of baculovirus-expressed recombinant human ERα, baculovirus-expressed recombinant human ERβ, GST-fused AF1 of ERα, GST-fused Hinge domain of ERα, GST fused ATF2 protein, or baculovirus-expressed recombinant human AIB1 and active p38 beta (100 ng per 20 μL of total volume; Upstate Biotechology, Cat. #14–253).

Reactions for Optimization 2 were set up with 1×kinase buffer (as above) supplemented with various concentrations of γ-$^{32}$P ATP and a fixed amount of cold ATP (10 μM, 100 μM, and 200 μM). These reactions further contained and a constant amount (0.5 μg per 20 μL of total volume) of baculovirus-expressed recombinant human ERα, baculovirus-expressed recombinant human ERβ, or baculovirus-expressed recombinant human AIB1 and active p38 beta (as above).

These reactions under optimized conditions were incubated at 30° C. for 30 minutes and then terminated by adding 20 μL 3×SDS sample buffer (187.5 mM Tris-HCl (pH 6.8 at 25° C.), 6% w/v SDS, 30% glycerol, 150 mM DTT, 0.03% w/v bromophenol blue) to each and vortexing. Reactions were then spun for 30 seconds in a microcentrifuge. Samples were heated to 95–100° C. for 2–5 minutes and loaded (20 μL per well) on a SDS-PAGE gel (10%).

Following electrophoresis, each gel was fixed with 60% methanol 10% acetic acid for 30 minutes and then stained with Coomassie Blue for 15 minutes. Gels were destained with 10% methanol 10% acetic acid for 2 hours and dried at 70° C. for 1 hour in a vacuum dryer. Dried gels were exposed to x-ray film and spot intensities were quantitated.

Example 4

The invention further provides data indicating the specific sites on the estrogen receptor that may be phosphorylated by p38. Recombinant p38 MAPK was expressed and purified according to the method of Cuenda A, 1996, EMBO J. 15(16):4156–4164. The AF1 and Hinge domains of the ER were expressed as GST fusion constructs in baculovirus. Fusion proteins were purified and these domains were then assayed according to the in vitro phosphorylation assay of Example 3.

Figure 3:
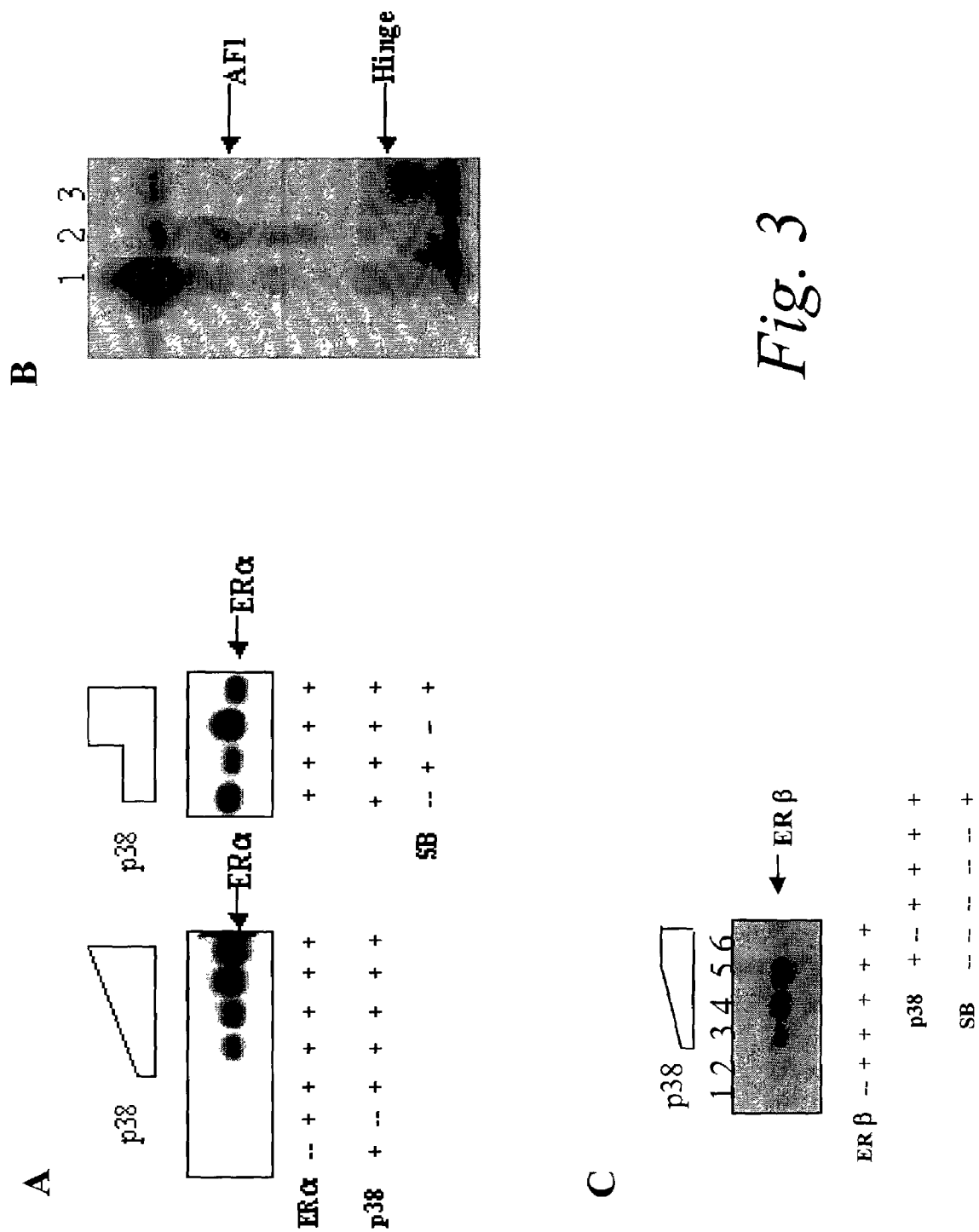
FIG. 3: In vitro phosphorylation of ERα by p38 MAPK. Panel A shows increasing doses of purified (recombinant) p38 MAP kinase phosphorylate baculovirus-expressed ERα. "SB"—p38-specific inhibitor SB 203580. Panel B shows phosphorylation of GST-fusion constructs of the AF1 and Hinge domains of the ER by recombinant p38 MAPK. Panel C shows phosphorylation of ERβ.

FIG. 3A shows that increasing doses of purified (recombinant) p38 MAP kinase phosphorylate baculovirus-expressed ERα. This phosphorylation is inhibited in the presence of the p38-specific inhibitor SB 203580 (FIG. 3A).

FIG. 3B shows that both AF1 (lane 2) and Hinge (lane 3) were phosphorylated by in vitro p38 MAP kinase. Lane 1 shows the autophosphorylation of p38 without substrate, which also appears in lane 2 & 3 at lower intensity.

FIG. 3C shows the results of incubating reactions containing 0.5 μg recombinant human ERβ, 1 μCi γ-$^{32}$P ATP, 100 μM ATP in 1×kinase buffer (as above) with or without SB 203580 at 0.5 μM, and with or without active p38β(see as above) (at 50 ng for lane 1 & 3; 100 ng for lane 4; 200 ng for lane 5 & 6. Zero for lane 2 under optimized conditions.

Using the in vitro kinase assay of Example 3, the present inventors have observed that all forms of p38 MAPK (alpha, beta, gamma, and delta) phosphorylate both ERα and ERβ and that the p38α- and p38β-induced phosphorylation of ER can be inhibited by the p38 specific inhibitor SB 203580.

Example 5

The instant invention provides in vitro data showing that p38 MAPK is capable of functionally activating ER not only by direct phosphorylation of ER, but also by phosphorylating the ER coactivator, Amplified in Breast Cancer 1 (AIB1).

Figure 4:
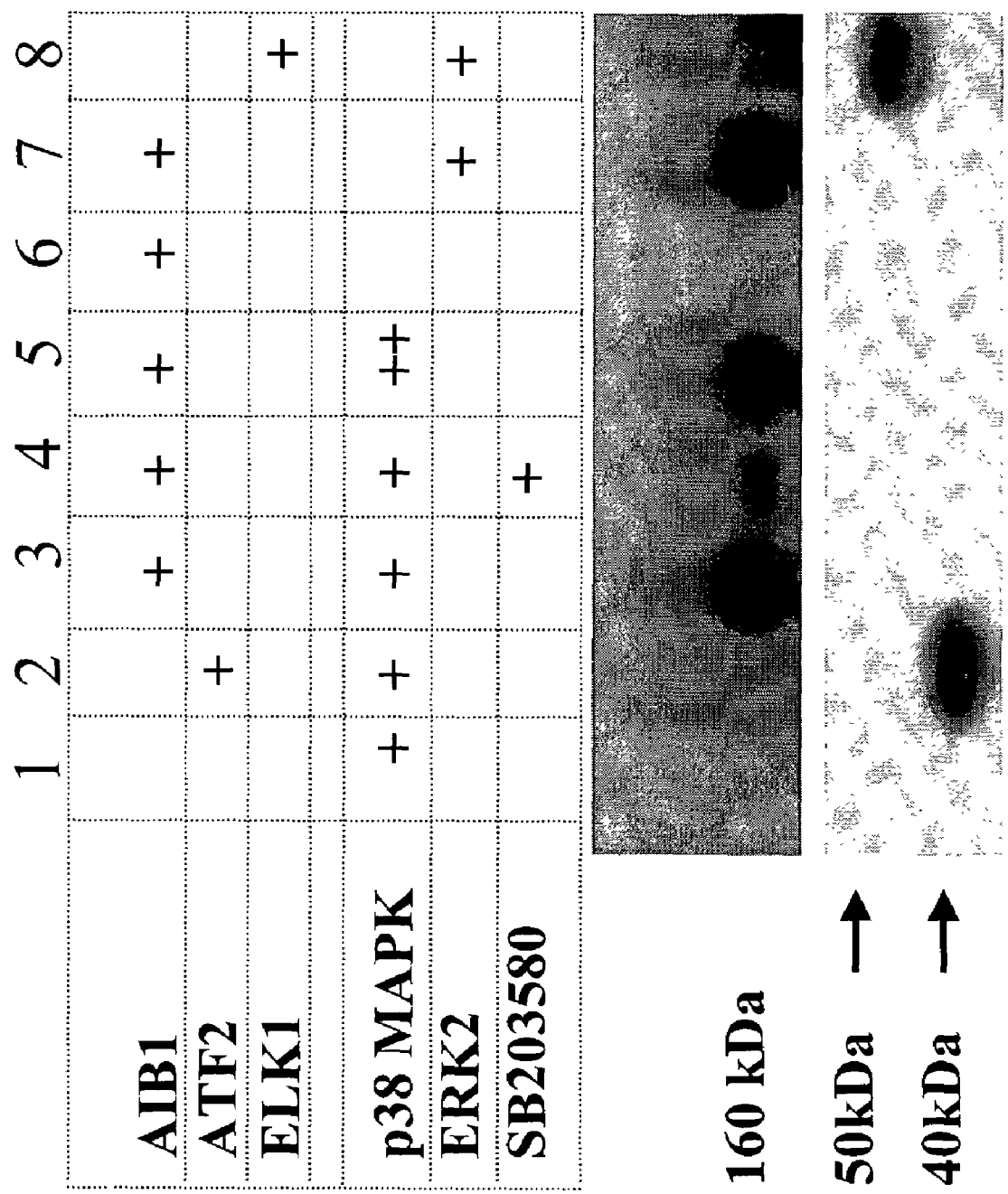
FIG. 4: In vitro phosphorylation of *Xenopus* oocyte-expressed AIB1 by p38 MAPK.

FIG. 4 shows in vitro phosphorylation (assay according to Example 3) of AIB1 by p38 MAPK. Purified (recombinant) p38 MAP kinase phosphorylates Xenopus oocyte-expressed AIB1 (Lanes 3,5) similarly to Extracellular Signal-Regulated Kinase 2 (ERK 2)(lane 7). The p38-specific inhibitor SB 203580 inhibits AIB1 phosphorylation by p38 MAPK (lane 4). Lanes 2 and 8 are positive controls for p38 MAPK and ERK kinase reaction with the known substrates Activating Transcription Factor 2 (ATF2) and ETS-like Transcription Factor-1 (ELK1), respectively.

These results indicate that p38 MAPK is able to phosphorylate ER coactivator AIB1. Therefore, p38 MAPK inhibitors may ameliorate, suppress, prevent or eliminate tamoxifen resistance and/or endocrine resistance, in part, by preventing AIB1 phosphorylation and, in part, by blocking p38 MAPK-mediated phosphorylation of ER.

Example 6

According to this example, high AIB1 correlated with a reduction in disease-free survival in patients receiving tamoxifen, indicative of tamoxifen resistance. AIB1 is activated by ERK1,2 MAPKs. When expression of AIB1 and HER-2, which activates ERK1,2 MAPKs, are considered together, only those patients whose tumors contained both high AIB1 and high HER-2 are resistant to tamoxifen. The antitumor activity of tamoxifen in patients with breast cancer is thus determined, in part, by tumor levels of AIB1, so that AIB1 may be an important new diagnostic and therapeutic target. See also WO 00/34788. In a similar way, the phosphorylation of AIB1 by p38 MAPK may have the same clinical importance and consequences.

The ER coactivator AIB1 is often amplified and overexpressed in breast tumors, and we have recently found that AIB1 is an important component of TamR found in Her2-overexpressing tumors. Interestingly, we found that both JNK and p38 MAPK can directly phosphorylate AIB1 in vitro. Thus, as has been suggested for growth factor signaling, AIB1 may also be a conduit for kinase-mediated stress signaling to the ER pathway. Our data suggests that increased active JNK and p38, and cross-talk between these pathways and the ER pathway, may play a key role in endocrine resistance through phosphorylation and activation of different components of the ER pathway. We are currently studying whether specific JNK and p38 inhibitors can circumvent endocrine resistance in vivo in our xenograft breast cancer model.

REFERENCES

The documents cited throughout this application are incorporated herein in their entirety by reference. Citation of these documents is not to be construed as an admission that such documents are available as "prior art" against the instant invention.

We claim:

1. A method of diagnosing a tamoxifen-resistant breast tumor in an individual comprising:
   providing a biological sample from the individual, and
   detecting p38 MAPK activity within said sample,
   wherein higher p38 MAPK activity in said biological sample compared to a sample obtained from a tamoxifen-sensitive breast tumor indicates that said biological sample is more tamoxifen resistant than the tamoxifen-sensitive breast tumor.

2. The method of claim 1 wherein the biological sample is derived from a tissue biopsy.

3. The method of claim 1 wherein the biological sample is obtained from a tumor.

4. The method of claim 1 wherein p38 MAPK activity is detected by a phosphorylation assay.

5. The method of claim 1 wherein said tumor is a human tumor.

6. The method of claim 1 wherein providing a biological sample from the individual further comprises biopsying tissue from the individual.

7. The method of claim 1 wherein providing a biological sample from the individual further comprises presenting a biological sample for analysis within its native in vivo context.

8. The method of claim 1 wherein the biological sample comprises cells.

9. The method of claim 1 wherein the biological sample comprises a bodily fluid.

10. The method of claim 1 wherein the biological sample comprises a bodily tissue.

11. The method of claim 1 wherein the biological sample comprises an organ.

12. The method of claim 1 wherein detecting p38 MAPK activity further comprises detecting p38 MAPK-dependent phosphorylation of a protein selected from the group consisting of amplified in breast cancer 1 (AIB1), activating transcription factor 2 (ATF-2), estrogen receptor α (ERα), estrogen receptor β (ERβ), mitogen activated protein kinase activated protein kinase 2 (MAPKAP-K2), MAPKAP-K3, p38-related/activated protein kinase (PRAK), and fragments thereof that include a p38 MAPK-dependent phosphorylation site.

13. The method of claim 1 wherein detecting p38 MAPK activity further comprises detecting p38 MAPK-dependent phosphorylation of a protein selected from the group consisting of Menkes copper transporting P-type ATPase (MNK), mitogen- and stress-activated protein kinase (MSK), ribosomal S6 kinase B (RSK-B), signal transducer and activator of transcription 1 (STAT 1), Max/Myc complex, Ets-like transcription factor-1 (Elk1), C/EBP homologous protein (CHOP), myocyte enhancer factor 2 (MEF2), and fragments thereof that include a p38 MAPK-dependent phosphorylation site.

14. A method of diagnosing an estrogen withdrawal-resistant breast tumor in an individual comprising:
providing a biological sample from the individual, and detecting p38 MAPK activity within said sample,
wherein higher p38 MAPK activity in said biological sample compared to a sample obtained from an estrogen withdrawal-sensitive breast tumor indicates that said biological sample is more estrogen withdrawal-resistant than the estrogen withdrawal-sensitive breast tumor.

15. The method of claim 14 wherein the biological sample is derived from a tissue biopsy.

16. The method of claim 14 wherein the biological sample is obtained from a tumor.

17. The method of claim 14 wherein p38 MAPK activity is detected by a phosphorylation assay.

18. The method of claim 14 wherein said tumor is a human tumor.

19. The method of claim 14 wherein providing a biological sample from the individual further comprises biopsying the biological sample from the individual.

20. The method of claim 14 wherein providing a biological sample from the individual further comprises presenting a biological sample for analysis within its native in vivo context.

21. The method of claim 14 wherein the biological sample comprises cells.

22. The method of claim 14 wherein the biological sample comprises a bodily fluid.

23. The method of claim 14 wherein the biological sample comprises a bodily tissue.

24. The method of claim 14 wherein the biological sample comprises an organ.

25. The method of claim 14 wherein detecting p38 MAPK activity further comprises detecting p38 MAPK-dependent phosphorylation of a protein selected from the group consisting of amplified in breast cancer 1 (AIB1), activating transcription factor 2 (ATF-2), estrogen receptor α (ERα), estrogen receptor β (ERβ), mitogen activated protein kinase activated protein kinase 2 (MAPKAP-K2), MAPKAP-K3, p38-related/activated protein kinase (PRAK), and fragments thereof that include a p38 MAPK-dependent phosphorylation site.

26. The method of claim 14 wherein detecting p38 MAPK activity further comprises detecting p38 MAPK-dependent phosphorylation of a protein selected from the group consisting of Menkes copper transporting P-type ATPase (MNK), mitogen- and stress-activated protein kinase (MSK), ribosomal S6 kinase B (RSK-B), signal transducer and activator of transcription 1 (STAT1), Max/Myc complex, Ets-like transcription factor-1 (Elk1), C/EBP homologous protein (CHOP), myocyte enhancer factor 2 (MEF2), and fragments thereof that include a p38 MAPK-dependent phosphorylation site.

27. The method of claim 4 wherein the phosphorylation assay is an in-gel kinase assay.

28. The method of claim 4 wherein the phosphorylation assay is a Western blot.

29. The method of claim 1 wherein providing a biological sample from the individual further comprises resecting tissue from the individual.

30. The method of claim 12 wherein the protein is amplified in breast cancer 1 (AIB1) or a fragment thereof that includes a p38 MAPK-dependent phosphorylation site.

31. The method of claim 12 wherein the protein is estrogen receptor α (ERα) or a fragment thereof that includes a p38 MAPK-dependent phosphorylation site.

32. The method of claim 12 wherein the protein is estrogen receptor β (ERβ) or a fragment thereof that includes a p38 MAPK-dependent phosphorylation site.

33. The method of claim 17 wherein the phosphorylation assay is an in-gel kinase assay.

34. The method of claim 17 wherein the phosphorylation assay is an Western blot assay.

35. The method of claim 14 wherein providing a biological sample from the individual further comprises resecting tissue from the individual.

36. The method of claim 25 wherein the protein is amplified in breast cancer 1 (AIB1) or a fragment thereof that includes a p38 MAPK-dependent phosphorylation site.

37. The method of claim 25 wherein the protein is estrogen receptor α(ERα) or a fragment thereof that includes a p38 MAPK-dependent phosphorylation site.

38. The method of claim 25 wherein the protein is estrogen receptor β (ERβ) or a fragment thereof that includes a p38 MAPK-dependent phosphorylation site.

* * * * *